United States Patent
Schwarzer et al.

(10) Patent No.: US 6,979,743 B1
(45) Date of Patent: Dec. 27, 2005

(54) PROCESSES FOR PREPARING PHYTOSTEROLS AND SUBSTANTIALLY CITROSTADIENOL-FREE PHYTOSTEROLS PREPARED THEREBY

(75) Inventors: Joerg Schwarzer, Hilden (DE); Bernhard Gutsche, Hilden (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/913,377

(22) PCT Filed: Feb. 4, 2000

(86) PCT No.: PCT/EP00/00903

§ 371 (c)(1),
(2), (4) Date: Nov. 13, 2001

(87) PCT Pub. No.: WO00/47570

PCT Pub. Date: Aug. 17, 2000

(30) Foreign Application Priority Data

Feb. 13, 1999 (DE) ................. 199 06 551

(51) Int. Cl.[7] ............................... C07D 9/00

(52) U.S. Cl. ..................... 552/545; 552/544

(58) Field of Search ............... 552/545, 544; 514/182, 170

(56) References Cited

U.S. PATENT DOCUMENTS

| 3,335,154 A | | 8/1967 | Smith | |
|---|---|---|---|---|
| 4,153,622 A | * | 5/1979 | Lamminkari et al. | 552/545 |
| 4,298,539 A | * | 11/1981 | Koskenniska | 552/545 |
| 4,422,974 A | | 12/1983 | Hamunen | |
| 4,963,346 A | * | 10/1990 | Amer | 424/49 |
| 5,487,817 A | | 1/1996 | Fizet | |
| 5,627,289 A | | 5/1997 | Jeromin et al. | |
| 6,107,456 A | * | 8/2000 | Huibers et al. | 530/205 |

FOREIGN PATENT DOCUMENTS

| DE | 32 26 225 A1 | | 2/1983 |
|---|---|---|---|
| DE | 42 28 476 A1 | | 3/1994 |
| EP | 0 333 472 B1 | | 9/1989 |
| EP | 0 656 894 B1 | | 2/1998 |
| EP | 0 610 742 B1 | | 3/1999 |
| GB | 2 145 079 A | | 3/1985 |
| WO | WO 95/04731 | * | 2/1995 |

* cited by examiner

*Primary Examiner*—Barbara P. Badio
(74) *Attorney, Agent, or Firm*—John F. Daniels, III; Daniel S. Ortiz

(57) ABSTRACT

Processes for preparing substantially citrostadienol-free phytosterols are disclosed. The processes described include dissolving a liquid phytosterol in a hydrocarbon solvent, optionally with added methanol, and crystallizing the phytosterol compounds. Also described are the resulting phytosterols which are substantially citrostadienol-free, and preferably contain less than 0.5% by weight citrostadienol.

26 Claims, No Drawings

PROCESSES FOR PREPARING PHYTOSTEROLS AND SUBSTANTIALLY CITROSTADIENOL-FREE PHYTOSTEROLS PREPARED THEREBY

This application is a 371 of PCT/EP00/00903 filed Feb. 4, 2000.

BACKGROUND OF THE INVENTION

Phytosterols and their esters possess hypocholesterolaemic properties, i.e. these substances are capable of lowering the cholesterol level in the blood. Accordingly, they are used as food additives, for example for the production of margarine, frying oils, sausage, ice cream and the like. The production of sterols and other unsaponifiable constituents, such as tocopherols for example, from distillates obtained in the deacidification of vegetable oils, has already been variously described in the literature, cf. EP-A2 0 610 742 (Hoffmann-LaRoche), GB-A1 U.S. Pat. No. 2,145,079 (Nisshin Oil Mills Japan) and EP-A1 0 333 472 (Palm Oil Research and Development Board).

European Patent EP-B1 0 656 894 (Henkel) describes a process for the production of sterols in which a residue from the distillation of methyl esters consisting essentially of glycerides, sterols, sterol esters and tocopherols is transesterified with methanol in the presence of alkaline catalysts. After neutralization of the catalyst, removal of the excess methanol by distillation and, optionally, removal of the catalyst by washing, the sterols are crystallized by lowering the reaction temperature from about 65 to 20° C. The crystals obtained are then washed with methanol and water. However, where residues from the production of methyl esters based on sunflower oil are used, the sterols obtained contain not only the target components, such as above all campesterol, campestanol, stigmasterol, β-sitosterol and β-sitostanol, but also significant amounts of citrostadienol which is undesirable for applicational reasons. German patent application DE-A1 3226225 (Raisio) describes a process by which the amount of citrostadienol can be reduced. In this process, the solid sterols are first dissolved in heptane and then re-crystallized after addition of methanol. However, the resulting products are by no means free from citrostadienol and, in addition, the yields are unsatisfactory.

Accordingly, the problem addressed by the present invention was to provide high yields of phytosterols which would be distinguished above all by the fact that they would be largely free from citrostadienol.

BRIEF SUMMARY OF THE INVENTION

The present invention relates, in general, to food additives and phytosterols for use therein, and more particularly, to a new process for the production of phytosterols substantially free from citrostadienol.

The present invention relates to a process for the production of phytosterols by alkali-catalyzed transesterification of residues from the production of methyl esters with methanol, neutralization of the catalyst and removal of the unreacted alcohol, characterized in that the transesterification products are dissolved in saturated hydrocarbons containing 5 to 10 carbon atoms at a temperature at which they are present in liquid form, the phytosterols are crystallized in the hydrocarbon by lowering the temperature, optionally after the addition of an adequate quantity of aqueous methanol, and are then removed and purified in known manner by filtration, washing and drying.

It has surprisingly been found that crystallization of the sterols in hydrocarbons coupled with the addition of effective quantities of aqueous methanol gives products which have citrostadienol contents below 0.5% by weight and preferably below 0.2% by weight and which are therefore substantially free from this unwanted component. Another advantage is that, in contrast to known processes, the yields of sterol in the crystallization step are significantly higher.

DETAILED DESCRIPTION OF THE INVENTION

The production of a sterol-rich fraction by transesterification of residues from the deacidification of vegetable oils and subsequent working up can be carried out as described in EP-B1 0 656 894. Suitable starting materials are the distillation residues obtained, for example, as so-called deodorizer condensates in the production of fatty acid methyl esters based on rapeseed oil or, more particularly, sunflower oil. Tall oil pitch, more particularly pitch obtained from birch bark, is also suitable. Where it relates to the production of the sterol fractions, reference is comprehensively made to the document cited above.

Crystallization

A key feature of the new process is that the products obtainable from the transesterification are dissolved in the hydrocarbons at a temperature at which they are still liquid. This is preferably the case at 60 to 80° C. and more particularly at 65 to 70° C. Suitable solvents are lower alkanes, for example pentane, hexane, heptane, octane, nonane and decane. Included herein are both the linear hydrocarbons and the branched structural isomers derived therefrom and mixtures thereof. However, the use of hexane, heptane or mixtures thereof has proved to be particularly advantageous. After the sterols have dissolved, the temperature is reduced to such a value that the pure sterols crystallize. It has proved to be of advantage in this regard to add an effective quantity of aqueous methanol to the mixture. 1 to 25% by weight aqueous methanol solutions are normally used for this purpose, the quantity in which they are added—based on the hydrocarbons—typically being in the range from about 1 to 15% by weight. Although the crystallization process begins at a temperature as low as about 30° C., it has proved to be of advantage to lower the temperature to about 15 to 25° C. The phytosterols obtained are then removed and purified in known manner, i.e. filtered off, washed free from soaps and then dried to constant weight. The resulting products have a citrostadienol content of less than 0.5% by weight and preferably less than 0.2% by weight.

EXAMPLES

Example 1

200 g of a distillation residue from the production of sunflower oil fatty acid methyl ester containing inter alia 15% by weight of glycerides and 28% by weight of free or bound sterols were introduced together with 78 g of methanol into a 1-liter three-necked condenser equipped with a stirrer and distillation head. 3.8 g of 30% by weight sodium methylate solution were then added to the mixture, followed by stirring for 4 h at 70° C. The alkaline catalyst was then neutralized by addition of 4.2 g of citric acid dissolved in 19 g of methanol, the unreacted methanol was distilled off in vacuo and the residue was washed soap-free with water at 65° C. A mixture of 400 g of hexane, 26 g of methanol and 8 g of water was added to the crude product and the whole was cooled to 20° C. Removal of the mother liquor through a filter and drying of the residue left 41 g of sterols which were free from citrostadienol.

Example 2

The procedure was as described in Example 1 except that a mixture of 200 g of heptane, 13 g of methanol and 4 g of water was added to 100 g of the transesterification product and the whole was cooled for 4 hours to 20° C. Filtration and drying left 19.4 g of sterols with a citrostadienol content of less than 0.2% by weight.

Comparison Example C1

The procedure was as described in Example 1 except that methanol was added to the transesterification product in a ratio by weight of 1:1. On cooling to 20° C., the crystals precipitated and were filtered off, washed with aqueous methanol and then dried. However, the resulting sterols still contained 4.7% by weight of citrostadienol. 100 g of this product were dissolved in heptane at 70° C. and, after the addition of 20 g of methanol, the whole was again cooled for 4 hours to a temperature of 20° C. Filtration and drying left only 75 g of sterols still with a citrostadienol content of 4.2% by weight.

What is claimed is:

1. A process for preparing phytosterols, said process comprising:
    (a) providing a liquid phytosterol starting material obtained by transesterification of a distillation residue with an alkanol;
    (b) dissolving the liquid phytosterol starting material in a hydrocarbon solvent; and
    (c) crystallizing a phytosterol product, wherein the phytosterol product is substantially citrostadienol-free.
2. The process according to claim 1, wherein the distillation residue comprises a deodorizer condensate obtained from fatty acid methyl ester production.
3. The process according to claim 2, wherein the deodorizer condensate is derived from an oil selected from the group consisting of rapeseed oil and sunflower oil.
4. The process according to claim 3, wherein the oil comprises sunflower oil.
5. The process according to claim 1, wherein the distillation residue comprises tall oil pitch.
6. The process according to claim 1, wherein the alkanol comprises methanol.
7. The process according to claim 3, wherein the alkanol comprises methanol.
8. The process according to claim 1, wherein the liquid phytosterol starting material is maintained at a temperature of from 60° C. to 80° C. prior to and during dissolution in the hydrocarbon solvent.
9. The process according to claim 3, wherein the liquid phytosterol starting material is maintained at a temperature of from 60° C. to 80° C. prior to and during dissolution in the hydrocarbon solvent.
10. The process according to claim 8, wherein the liquid phytosterol starting material is maintained at a temperature of from 65° C. to 70° C.
11. The process according to claim 9, wherein the liquid phytosterol starting material is maintained at a temperature of from 65° C. to 70° C.
12. The process according to claim 1, wherein the hydrocarbon solvent comprises a linear or branched alkane isomer selected from the group consisting of pentane, hexane, heptane, octane, nonane, decane, and mixtures thereof.
13. The process according to claim 1, wherein the hydrocarbon solvent comprises a linear or branched alkane isomer selected from the group consisting of hexane, heptane, and mixtures thereof.
14. The process according to claim 1, wherein methanol is combined with the hydrocarbon solvent prior to crystallization.
15. The process according to claim 14, wherein the methanol is present in an amount of from 1 to 15% by weight, based on the hydrocarbon solvent.
16. The process according to claim 3, wherein methanol is combined with the hydrocarbon solvent prior to crystallization.
17. The process according to claim 16, wherein the methanol is present in an amount of from 1 to 15% by weight, based on the hydrocarbon solvent.
18. The process according to claim 8, wherein methanol is combined with the hydrocarbon solvent prior to crystallization.
19. The process according to claim 18, wherein the methanol is present in an amount of from 1 to 15% by weight, based on the hydrocarbon solvent.
20. The process according to claim 1, wherein crystallizing the phytosterol product comprises cooling the liquid phytosterol starting material in the hydrocarbon solvent to a temperature of below about 30° C.
21. The process according to claim 1, wherein crystallizing the phytosterol product comprises cooling the liquid phytosterol starting material in the hydrocarbon solvent to a temperature of from about 25° C. to about 30° C.
22. The process according to claim 3, wherein crystallizing the phytosterol product comprises cooling the liquid phytosterol starting material in the hydrocarbon solvent to a temperature of below about 30° C.
23. The process according to claim 3, wherein crystallizing the phytosterol product comprises cooling the liquid phytosterol starting material in the hydrocarbon solvent to a temperature of from about 25° C. to about 30° C.
24. The process according to claim 1, wherein the phytosterol product has a citrostadienol content of less than 0.5% by weight.
25. The process according to claim 1, wherein the phytosterol product has a citrostadienol content of less than 0.2% by weight.
26. A process for preparing phytosterols, said process comprising:
    (a) providing a liquid phytosterol starting material obtained by transesterification of a distillation residue with methanol, wherein the distillation residue comprises a deodorizer condensate derived from sunflower oil;
    (b) dissolving the liquid phytosterol starting material in a hydrocarbon solvent, the hydrocarbon solvent comprising a linear or branched alkane isomer selected from the group consisting of hexane, heptane, and mixtures thereof, wherein the liquid phytosterol starting material is maintained at a temperature of from 60° C. to 80° C. prior to and during dissolution in the hydrocarbon solvent; and (c) crystallizing a phytosterol product via cooling the liquid phytosterol starting material in the hydrocarbon solvent to a temperature of below about 30° C., wherein methanol is combined with the hydrocarbon solvent prior to crystallization in an amount of from 1 to 15% by weight, based on the hydrocarbon solvent, and wherein the phytosterol product has a citrostadienol content of less than 0.5% by weight.

* * * * *